United States Patent
Paik et al.

(10) Patent No.: US 9,977,023 B2
(45) Date of Patent: May 22, 2018

(54) PROBES AND METHODS FOR THE DETECTION OF A VIRUS THAT CAUSES ACUTE ENTERITIS

(71) Applicant: Catholic University Industry Academic Cooperation Foundation, Seoul (KR)

(72) Inventors: Soon-young Paik, Dongjak-gu Seoul (KR); Yu-jeong Won, Dongdaemun-gu Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 0 days. days.

(21) Appl. No.: 15/531,618

(22) PCT Filed: Nov. 26, 2015

(86) PCT No.: PCT/KR2015/012777
§ 371 (c)(1),
(2) Date: May 30, 2017

(87) PCT Pub. No.: WO2016/085267
PCT Pub. Date: Jun. 2, 2016

(65) Prior Publication Data
US 2017/0356912 A1    Dec. 14, 2017

(30) Foreign Application Priority Data

Nov. 28, 2014  (KR) .................. 10-2014-0168202

(51) Int. Cl.
| | | |
|---|---|---|
| *G01N 33/569* | (2006.01) | |
| *C12Q 1/68* | (2018.01) | |
| *C12Q 1/70* | (2006.01) | |
| *C12N 7/00* | (2006.01) | |

(52) U.S. Cl.
CPC ......... *G01N 33/56983* (2013.01); *C12Q 1/68* (2013.01); *C12Q 1/701* (2013.01); *C12N 7/00* (2013.01)

(58) Field of Classification Search
None
See application file for complete search history.

(56) References Cited

U.S. PATENT DOCUMENTS

2003/0129588 A1    7/2003  Estes et al.

FOREIGN PATENT DOCUMENTS

| KR | 1020010076794 A | 8/2001 |
| KR | 1020080088279 A | 10/2008 |
| KR | 101377824 B1 | 4/2014 |
| KR | 1020140110342 A | 9/2014 |

OTHER PUBLICATIONS

International Search Report and Written Opinion and English Translation thereof for International Application No. PCT/KR2015/012777 dated Mar. 4, 2016, 16 pages.

*Primary Examiner* — Nicole Kinsey White
(74) *Attorney, Agent, or Firm* — Hoffman Warnick LLC

(57) ABSTRACT

The present invention relates to a composition comprising a probe for detecting six representative causative viruses of acute enteritis (norovirus genogroup I and genogroup II, rotavirus, hepatitis A virus, coxsackievirus, astrovirus, and adenovirus), and a DNA microarray, a kit, and a detection method comprising the composition. The present invention is effective due to high specificity and sensitivity to viruses. In addition, since the causative viruses can simply be detected at low cost compared to conventional detection methods, without expensive diagnosis devices or specialists, the present invention may be effectively used as a method for diagnosing viruses causing acute enteritis.

8 Claims, 5 Drawing Sheets

| Probe | Sequence | Target | Size, GC, Tem | Seq. No. |
|---|---|---|---|---|
| Norovirus type I | GGA CAG GAG ATC GCA ATC TCC TGC CCG AAT TYG TAA ATG ATG ATG GCG TCT AAG GAC | RdRp/VP1 | 57mer, 50%, 74 | 1 |
| Norovirus type II | CTA TGT TCC CCC AYA TAA TAG TRG ATG TTA GGC AAY TGG AAC CTG TGT TGA TCC CCT TAC C | RdRp/VP1 | 61mer, 45%, 73 | 2 |
| Rotavirus | RTG TAM WSA ATA TAT WAA YAM YGG KYT RCC ACC AAT KCA RAA TAC DAG RAA TRT WGT WCC | VP7 | 60mer, 40%, 72 | 3 |
| HAV | CTG GVA GRT TGG TGA GRK TBA ATG ATG AAA AAT GGA CAG AAA TGA AAG ATG A | VP1/2A | 52mer, 35%, 69 | 4 |
| Coxsackievirus | GGC ARA CDT CCA CRA AYC CHA GYG TBT TYT GGA CAG ARG GDA ATG CMC CAC CVN GBA TG | VP1 | 59mer, 45%, 80 | 5 |
| Astrovirus | GAG GAT ACY AGR GTR ATA CAY ATA ACT GCA ACT GAR AAR AAY ACW GAT TCH ACV CCW GC | ORF1b(RdRp) | 59mer, 37%, 73 | 6 |
| Adenovirus | SAW ACC AGC CCM ATG YWR CCA TGT TAY GGG TCW TAC GCY ARA CCA ACA AA | Hexon | 50mer, 45%, 74 | 7 |

FIG. 1

PROBES AND METHODS FOR THE DETECTION OF A VIRUS THAT CAUSES ACUTE ENTERITIS

This research was supported by grants from the "Development of Human Norovirus Vaccine Candidates and Animal Model," Korea Health Technology R&D Project through Korea Health Industry Development Institute (KHIDI) funded by Ministry of Health & Welfare, Republic of Korea in 2015.12.03~2018.11.30 (grant number: HI15C1781).

TECHNICAL FIELD

The present invention relates to a composition including a probe for detecting six representative types of viruses causing acute enteritis (norovirus genogroups I and II, rotavirus, hepatitis A virus, coxsackievirus, astrovirus, and adenovirus), a DNA microarray and a kit including the composition, and a detection method using the composition.

BACKGROUND ART

Enteric viruses generally refer to all types of viruses that may have serious medical effects because they primarily infect the gastrointestinal tract through the human mouth when the natural environments like water and soil are contaminated, and then spread to various sites in the body. In recent years, approximately 100 types of enteric viruses have been classified. Among these, the enteric viruses typically include norovirus, rotavirus, hepatitis A virus (HAV), coxsackievirus, astrovirus, adenovirus, etc.

Norovirus is a representative pathogen that causes food poisoning in the winter, and has a positive single-stranded RNA genome. It has been reported that norovirus causes at least 50% of waterborne and foodborne poisoning incidents which occurred between the years 2007 and 2009. Upon infection, its main symptoms include nausea, vomiting, stomachaches, diarrhea, pyrexia, etc. In rare cases, the elderly, patients, and the like may die from the effects of serious dehydration. The infection may be caused via a wide variety of routes of infection, that is, caused through interpersonal contact, feces, the mouth, and potential aerosol infectivity, and caused through contaminated water and foods, and there are a variety of virus variants. Concurrent infections by two or more variant noroviruses often occur when fish and shellfish are contaminated or water is contaminated.

Rotavirus is a virus that has a double-stranded RNA genome consisting of 11 segments, and causes rotavirus enteritis which annually kills more than 600,000 people worldwide. In general, infants under five years old are infected with rotavirus. Upon infection, its main symptoms include dehydration caused by a disorder such as acute diarrhea, and thus patients of developing and underdeveloped countries have a high death rate because the patients are not rehydrated when they have a symptom of dehydration. Rotavirus is a virus which has been regularly reported to the surveillance system run by the Korea Centers for Disease Control and Prevention.

Hepatitis A virus has a single-stranded RNA genome, and as a waterborne virus, is manifested by mild cold symptoms, jaundice or severe gastrointestinal symptoms such as stomachaches, vomiting, and diarrhea upon infection. The hepatitis A virus has become a big problem as its infections have surged in developed countries with good hygienic conditions. In the case of Korea, from 2005 to 2009, incidence has increased 19 fold, rapidly increasing from 789 in 2005, 2,081 in 2006, 2,233 in 2007, 7,895 in 2008, and to 15,041 in 2009. Waterborne viruses are generally found in age groups with weak immune systems, such as infants, the elderly, etc., but unusually, the age group of 20 to 30 accounts for 79% of hepatitis A virus incidence.

Coxsackievirus is a virus that has a single-stranded RNA genome and is usually transmitted through oral infection between young children in summer. Upon infection, its representative symptoms include gastrointestinal symptoms such as pyrexia and vomiting, diarrhea, etc. Sometimes, these symptoms develop into airway diseases such as pharyngitis, bronchitis, etc., central nervous system diseases such as nonpyogenic meningitis, encephalitis, paralysis, etc., exanthematous diseases on the mucosae or skin, myositis, or conjunctivitis.

Astrovirus has a positive single-stranded RNA genome and is manifested by rotavirus-like enteritis symptoms, which have been regularly reported to the surveillance system run by the Korea Centers for Disease Control and Prevention. Once infected, astrovirus has an incubation period of 34 days, and is manifested by accompanying symptoms such as shivering, diarrhea, headaches, vomiting, stomachaches, pyrexia, etc. In Korea, enteritis in young children is annually prevalent in fall and winter. It was analyzed that 28% of childhood diarrhea is caused by astrovirus.

Adenovirus is known to have a positive stranded DNA genome and cause a variety of diseases such as acute respiratory diseases, gastroenteritis, epidemic conjunctivitis, meningitis, and hemorrhagic cystitis, depending on serotype.

Such enteric viruses survive in natural ecosystems while maintaining their infectivity for a long time, and when such enteric viruses are released from a human body, the enteric viruses repeat the infection cycle in a human body. The viruses are easily spread because people are infected with a small amount of the viruses, and spread thorough tiny droplets of water, clothing or bedding, person-to-person transmission, or infections caused by contamination of surrounding environments occur easily, and secondary and tertiary infections also often occur via families or people around infected persons. Most enteroviral infections are caused by physical contact among people. The enteric viruses are detected in the mouth, larynx and intestines, and released from the human body in the form of oral secretions or feces. In general, the contamination (of hands, dinnerware, food, etc.) with the feces often becomes a source of infection, and saliva discharged by coughing may become a direct/indirect source of contamination.

The probability of mass food poisoning caused by the same source of contamination has increased with the development of the food service industry, a rise in national income, an increase in imported foods, the establishment and enlargement of group feeding systems, etc. Further, the food poisoning viruses may directly or indirectly cause additional social and financial problems because they have a rapid transmission rate of infection and may progress into a secondary infection. Last year, approximately 7,269 food poisoning patients in a total of 104 cases were reported in Korea (based on statistical data from the Korea Food & Drug Administration). Also, annually, three to five billion diarrhea patients are reported worldwide, and, among these, approximately 10 million patients die. In particular, diarrhea is a real problem because diarrhea is not a disorder having severe symptoms like influenza or tuberculosis but it affects daily life and industrial activities, resulting in serious economic losses.

A method of rapidly diagnosing a causative virus (an etiologic agent) is required to prevent such additional infections and treat patients at an early stage. However, it is difficult to identify an etiologic agent since symptoms are similar in the case of acute enteritis. Currently used methods of diagnosing a virus causing acute enteritis include a cell culture method, a method based on an antigen-antibody reaction, a gene identification method, etc., but have a drawback in that they require expensive equipment, specialists, and costs, and have problems such as reduced sensitivity, outbreaks of mutants, a long-term trial period, etc.

Therefore, there is a need for development of a method of rapidly and accurately detecting viruses causing acute enteritis at low cost without any additional devices.

DISCLOSURE

Technical Problem

The present invention is designed to solve the problems such as a need for the aforementioned expensive equipment and specialists and the long-term trial period, and it is an object of the present invention to provide a composition including a probe for detecting six representative types of viruses causing acute enteritis (norovirus genogroups I and II, rotavirus, hepatitis A virus (HAV), coxsackievirus, astrovirus, and adenovirus), a DNA microarray and kit for detection including the composition, and a detection method.

However, technical problems to be solved by the present invention are not limited to the technical problems described above, and other technical problems not disclosed herein will be clearly understood from the following description.

Technical Solution

To solve the above problems, according to an aspect of the present invention, there is provided a composition for detecting one or more viruses causing acute enteritis, which are selected from the group consisting of norovirus types I and II, rotavirus G genotype, hepatitis A virus, coxsackievirus, astrovirus, and adenovirus, comprising one or more probes selected from the group consisting of:

i) a probe for detecting the norovirus types I and II consisting of polynucleotides set forth in SEQ ID NOs: 1 and 2, respectively;

ii) a probe for detecting the rotavirus G genotype consisting of a polynucleotide set forth in SEQ ID NO: 3;

iii) a probe for detecting the hepatitis A virus consisting of a polynucleotide set forth in SEQ ID NO: 4;

iv) a probe for detecting the coxsackievirus consisting of a polynucleotide set forth in SEQ ID NO: 5;

v) a probe for detecting the astrovirus consisting of a polynucleotide set forth in SEQ ID NO: 6; and vi) a probe for detecting the adenovirus consisting of a polynucleotide set forth in SEQ ID NO: 7.

According to one exemplary embodiment of the present invention, the probe may be characterized by having a 5' terminus labeled with biotin.

According to another aspect of the present invention, there is provided a DNA microarray for detecting one or more viruses causing acute enteritis, which are selected from the group consisting of norovirus types I and II, rotavirus G genotype, hepatitis A virus, coxsackievirus, astrovirus, and adenovirus. Here the composition may be spotted on the DNA microarray.

According to still another aspect of the present invention, there is provided a kit for detecting one or more viruses causing acute enteritis, which are selected from the group consisting of norovirus types I and II, rotavirus G genotype, hepatitis A virus, coxsackievirus, astrovirus, and adenovirus. Here, the kit includes the DNA microarray.

According to yet another aspect of the present invention, there is provided a method of detecting one or more viruses causing acute enteritis, which are selected from the group consisting of norovirus types I and II, rotavirus G genotype, hepatitis A virus, coxsackievirus, astrovirus, and adenovirus. Here, the method includes performing a hybridization reaction on a sample collected from a specimen using the composition.

Advantageous Effects

The composition including a probe for detecting viruses causing acute enteritis, the DNA microarray, the kit, and the detection method according to the present invention can be useful in detecting and diagnosing viruses through a hybridization method using probes designed for six representative viruses causing acute enteritis. Therefore, the present invention can be used in a method of rapidly diagnosing viruses causing acute enteritis at low cost without any additional devices or specialists, and is expected to be applied to the diagnosis of six viruses causing acute enteritis at the same time and also the development of vaccines in the future.

DESCRIPTION OF DRAWINGS

FIG. 1 is a table showing base sequences of probes designed to detect norovirus types I and II, rotavirus, hepatitis A virus, coxsackievirus, astrovirus, and adenovirus.

BEST MODE

Figure 2:
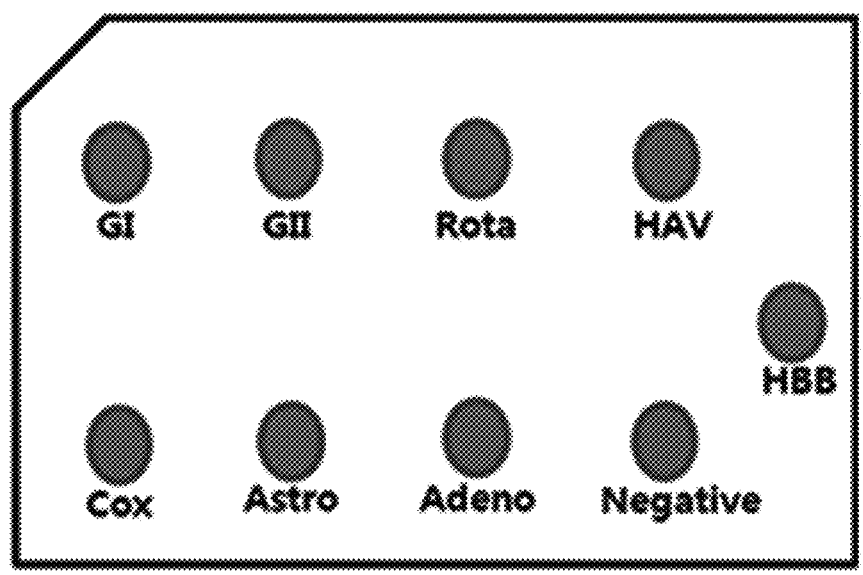
FIG. 2 is a schematic diagram showing probe spots for probe specificity tests through a hybridization reaction.

The present inventors have invented a composition including a probe for detecting six representative types of viruses causing acute enteritis (norovirus genogroups I and II, rotavirus, hepatitis A virus (HAV), coxsackievirus, astrovirus, and adenovirus), a DNA microarray and kit for detection including the composition, and a detection method, and confirmed that the composition including the probe, the DNA microarray, the kit, and the detection method respond specifically and sensitively to the respective viruses, and thus are effective in detecting the viruses through a hybridization reaction without any expensive equipment. Therefore, the present invention has been completed based on the above facts.

According to one exemplary embodiment of the present invention, viral DNA/RNA was respectively obtained from fecal samples positive for six viruses causing acute enteritis (see Example 1), and base sequences of the viral DNA/RNA thus obtained were compared to those of strains isolated in Korea and abroad to construct respective probes (see Example 2). Also, a specificity test using a hybridization reaction was performed to check whether each of the constructed probes (i.e., biotin-labeled probes) specifically reacts to each of the viruses. As a result, it was confirmed that each of the probes detected a target virus without any cross reactions (see Example 3). In addition, a sensitivity test using a hybridization reaction was performed to determine the minimum concentration of the virus detectable by each of the probes (i.e., biotin-labeled probes) whose specificity to the target virus was verified. As a result, it was confirmed that each of the probes detects the virus even when the virus is diluted to a concentration of 0.1 μg/μl (see Example 4).

Therefore, the present invention provides a composition for detecting one or more viruses causing acute enteritis, which are selected from the group consisting of norovirus types I and II, rotavirus G genotype, hepatitis A virus, coxsackievirus, astrovirus, and adenovirus. Here, the composition includes one or more probes selected from the group consisting of:

i) a probe for detecting the norovirus types I and II consisting of polynucleotides set forth in SEQ ID NOs: 1 and 2, respectively;

ii) a probe for detecting the rotavirus G genotype consisting of a polynucleotide set forth in SEQ ID NO: 3;

iii) a probe for detecting the hepatitis A virus consisting of a polynucleotide set forth in SEQ ID NO: 4;

iv) a probe for detecting the coxsackievirus consisting of a polynucleotide set forth in SEQ ID NO: 5;

v) a probe for detecting the astrovirus consisting of a polynucleotide set forth in SEQ ID NO: 6; and vi) a probe for detecting the adenovirus consisting of a polynucleotide set forth in SEQ ID NO: 7, but the present invention is not limited thereto.

In the composition of the present invention, the probe may be characterized by having a 5' terminus labeled with biotin, but the present invention is not limited thereto.

Also, a DNA microarray for detecting a virus causing acute enteritis, on which the composition is spotted, may be provided. Preferably, the virus causing acute enteritis may be selected from the group consisting of norovirus types I and II, rotavirus G genotype, hepatitis A virus, coxsackievirus, astrovirus, and adenovirus, but the present invention is not limited thereto.

In addition, a kit for detecting a virus causing acute enteritis, which includes the DNA microarray, may be provided. Preferably, the virus causing acute enteritis may be selected from the group consisting of norovirus types I and II, rotavirus G genotype, hepatitis A virus, coxsackievirus, astrovirus, and adenovirus, but the present invention is not limited thereto.

Further, a method of detecting a virus causing acute enteritis may be provided, which includes performing a hybridization reaction on a sample collected from a specimen using the composition including the probe according to the present invention. Preferably, the virus causing acute enteritis may be selected from the group consisting of norovirus types I and II, rotavirus G genotype, hepatitis A virus, coxsackievirus, astrovirus, and adenovirus, but the present invention is not limited thereto.

Hereinafter, preferred exemplary embodiments of the present invention will be described in order to aid in understanding the present invention. However, it should be understood that the description set forth herein is merely intended to provide a better understanding of the present invention and is not intended to limit the scope of the present invention.

EXAMPLES

Example 1

Collection of Positive Samples and Preparation of Viral DNA/RNA Samples 50 mg of each of fecal samples positive for norovirus genogroups I and II, rotavirus, hepatitis A virus, coxsackievirus, astrovirus, and adenovirus, all of which were provided by the Waterborne Virus Bank, was suspended in 500 μl of PBS, and the resulting suspension was vigorously vortexed for 30 minutes, and then centrifuged at 10,000 rpm for 10 minutes in a microcentrifuge. Thereafter, 140 μl of a supernatant was collected, and viral DNA/RNA was extracted using a viral DNA/RNA extraction kit. The extracted supernatant was transferred to a 1.5 ml tube, and 250 μl of a lysis buffer was added thereto. Then, the resulting mixture was mixed for 15 seconds (pulse-vortexing). The mixture was kept at room temperature for 10 minutes, and gently centrifuged to precipitate a pellet. Subsequently, 350 μl of a binding buffer was added thereto, and the mixture was mixed for 15 seconds, and gently centrifuged again. A RNA binding process was performed by putting the mixed sample into a spin column and centrifuging the sample at 13,000 rpm for one minute. In this case, 500 μl of a washing buffer A was added there to, and the sample was centrifuged at 13,000 rpm for one minute. The spin column was transferred to a new 2 ml tube, 500 μl of a washing buffer B was added thereto, and the mixed sample was centrifuged at 13,000 rpm for one minute. The spin column was again transferred to a new 2 ml tube, and centrifuged to complete one cycle. Then, the spin column was transferred to a 1.5 ml tube, and approximately 60 μl of an elution buffer was added thereto. Then, the mixed sample was kept at room temperature for one minute, and then centrifuged at 13,000 rpm for one minute to obtain viral DNA/RNA. The obtained viral DNA/RNA was stored at −70° C.

Example 2

Construction of Probes

To construct probes, base sequences of strains isolated in Korea or abroad were collected from NCBI, EMBL, and DDBJ. Based on the base sequences, the base sequences of the six viruses isolated in Example 1 were compared and analyzed using a Megalign program (DNAStar), and the probes were designed (FIG. 1).

Norovirus has a positive single-stranded RNA genome. In the whole genome (7.5 Kb) consisting of ORF1, ORF2, and ORF3, RdRp and VP1 regions known as conserved regions were targeted, and each of a 57 bp-sized genogroup I (GI.1-8) probe specific to RdRp and a 61 bp-sized genogroup II (GII.1-17) probe specific to VP1 was designed.

Rotavirus has a double-stranded RNA genome consisting of 11 segments. Among these, a base sequence of VP7 (G-16) which is an important part for determining a genotype and located at the outermost site of the rotavirus was analyzed to design a 60 bp-sized probe capable of detecting the rotavirus.

Hepatitis A virus (HAV) has a single-stranded RNA genome. Thus, a 52 bp-sized probe targeting a VP1/2A part was designed to detect all types of hepatitis A viruses.

Coxsackieviruses may be mainly divided into groups A and B. The coxsackie B virus, which mainly infects the human body, has a positive single-stranded RNA genome and 6 serotypes. Among these, a 59 bp-sized probe targeting a VP1 region of the coxsackie B virus was designed.

Astrovirus has a positive single-stranded RNA genome, and is composed of non-structural proteins (a viral serine protease and an RNA-dependent RNA polymerase) and capsid proteins. Among these, a base sequence of an ORF1b (RdRp) region known as a conserved region was analyzed to design a 59 bp-sized probe so as to detect all types of the astroviruses.

Adenovirus has a positive stranded DNA genome. Thus, a base sequence of Hexon known as a conserved region in the genome was analyzed to design a 50 bp-sized probe.

Also, the 5' terminus of each of the constructed probes was labeled with biotin.

Example 3

Specificity Test using Hybridization Reaction

A specificity test using a hybridization reaction was performed to check whether the biotin-labeled probes constructed in Example 2 specifically reacted with each of the viruses. In this case, hemoglobin beta (HBB) was used as the control.

As shown in FIG. 2, the viral DNA/RNA extracted in Example 1 was denatured at 95° C. for 10 minutes, and kept in ice for 5 minutes. Thereafter, 1μof the viral DNA/RNA was spotted on a nitrocellulose membrane, and banked at 80° C. for an hour to fix the DNA/RNA in the nitrocellulose membrane. Then, the nitrocellulose membrane was transferred to a hybridization solution (5× Denhardt's, 5×SSC, 0.1% SDS, 0.1 mg/ml denatured salmon sperm DNA, and a biotin-labeled probe) corresponding to each virus DNA/RNA, and hybridized at 65° C. for an hour. The hybridized nitrocellulose membrane was washed once with a 2× wash buffer (2×SSC, and 0.1% SDS), and again washed once with a 0.5× wash buffer (0.5×SSC, and 0.1% SDS). Then, the washed nitrocellulose membrane was detected using a biotin chromogenic detection kit. To do this, the nitrocellulose membrane was put into a blocking solution, and reacted for 30 minutes. Thereafter, the blocking solution was diluted by adding 75 mU/ml (1:5000) of a streptavidin-AP conjugate thereto. The nitrocellulose membrane was immersed in the diluted solution, reacted for 30 minutes, and then washed once with a 1× wash buffer for 15 minutes. The nitrocellulose membrane was put into a detection buffer, and reacted for 10 minutes. As a chromogenic substrate, a BCIP/NBT substrate solution was then added to the reaction mixture, and reacted for 20 minutes in a dark room to determine a level of a chromogenic reaction.

Figure 3:
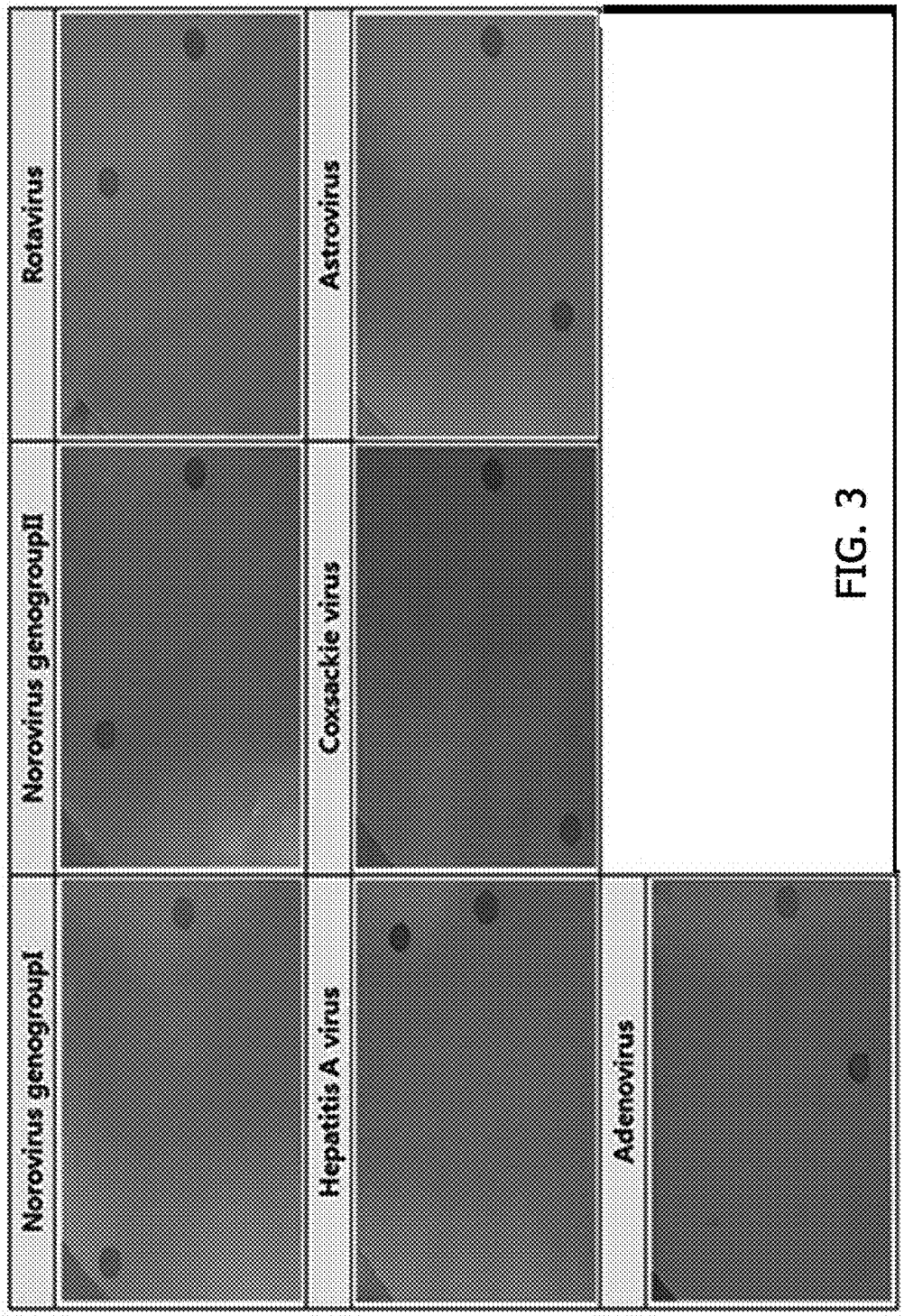
FIG. 3 is an image showing the result of the probe specificity tests through the hybridization reaction.

As a result, it was confirmed that each of the probes detected only the target virus without any cross reactions, as shown in FIG. 3.

Example 4

Sensitivity Test using Hybridization Reaction

A sensitivity test using a hybridization reaction was performed to determine the minimum concentration of the virus detectable by each of the probes (i.e., biotin-labeled probes) whose specificity to the target virus was confirmed in Example 3.

Figure 4:
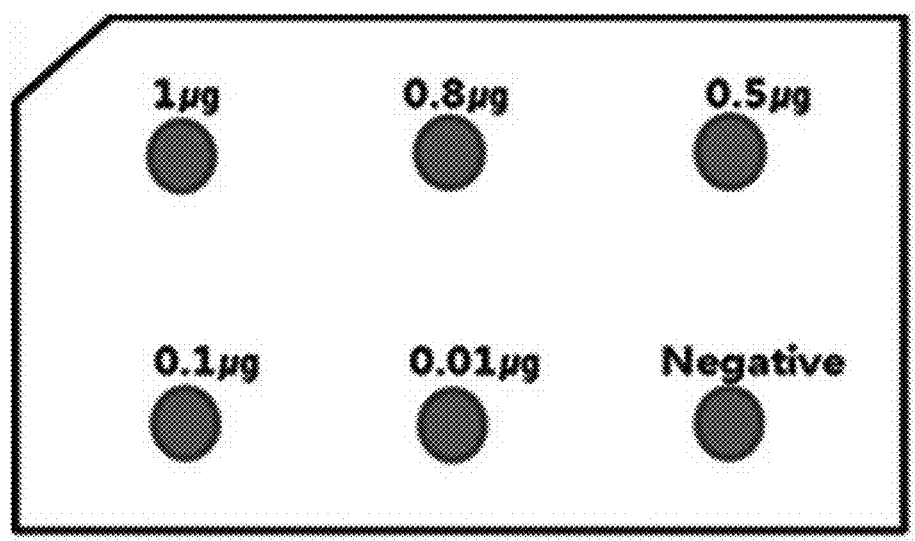
FIG. 4 is a schematic diagram showing probe spots for probe sensitivity tests through a hybridization reaction.

As shown in FIG. 4, each viral DNA/RNA extracted in Example 1 was diluted to a concentration of 1, 0.8, 0.5, 0.1, and 0.01 μg/μl, denatured at 95° C. for 10 minutes, and then kept in ice for 5 minutes. Thereafter, 1 μl of the viral DNA/RNA was spotted on a nitrocellulose membrane, and banked at 80° C. for an hour to fix the DNA/RNA in the nitrocellulose membrane. Subsequent processes such as hybridization, washing, and detection were performed in the same manner as in Example 3.

Figure 5:
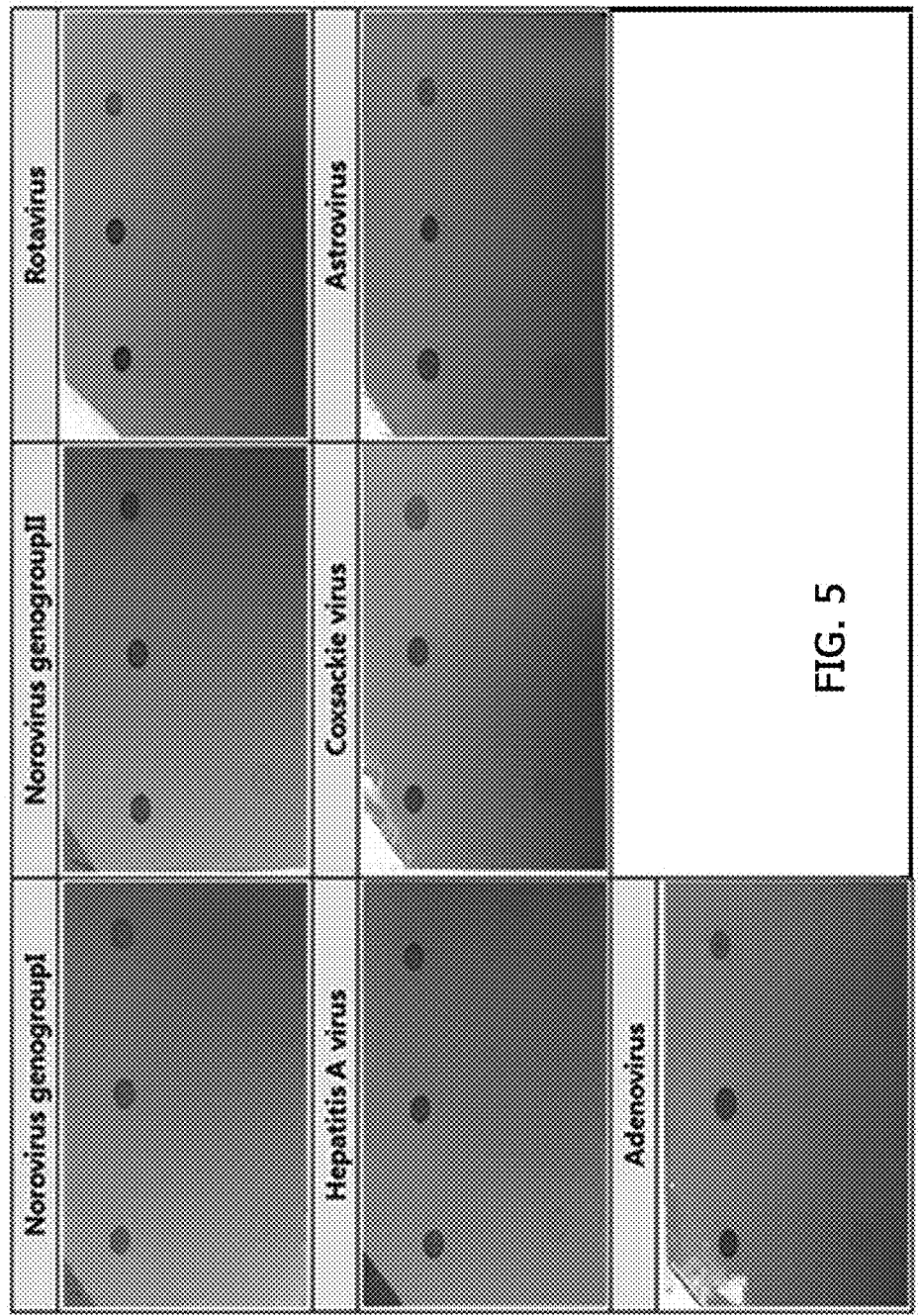
FIG. 5 is an image showing the result of the probe sensitivity tests through the hybridization reaction.

As a result, it was confirmed that, when the target virus was diluted to a concentration of 1 μg/μl, 0.8 μg/μl, 0.5 μg/μl, 0.1 μg/μl, and 0.01 μg/μl, each of the probes detected the target virus when present up to a dilution concentration of 0.1 μg/μl, as shown in FIG. 5.

Although the present invention presented herein has been disclosed for illustrative purposes, it should be understood to those skilled in the art to which the present invention pertains that various modifications and changes are possible without departing from the scope and spirit of the present invention. Therefore, the exemplary embodiments disclosed above are illustrative in all aspects, but not intended to limit the present invention.

The invention claimed is:

1. A composition for detecting one or more viruses selected from the group consisting of norovirus types I and II, rotavirus G genotype, hepatitis A virus, coxsackievirus, astrovirus, and adenovirus, comprising one or more probes selected from the group consisting of:
  i) a probe for detecting norovirus types I and II consisting of the polynucleotide set forth in SEQ ID NOs: 1 and 2, respectively;
  ii) a probe for detecting rotavirus G genotype consisting of the polynucleotide set forth in SEQ ID NO: 3;
  iii) a probe for detecting hepatitis A virus consisting of the polynucleotide set forth in SEQ ID NO: 4;
  iv) a probe for detecting coxsackievirus consisting of the polynucleotide set forth in SEQ ID NO: 5;
  v) a probe for detecting astrovirus consisting of the polynucleotide set forth in SEQ ID NO: 6; and
  vi) a probe for detecting adenovirus consisting of the polynucleotide set forth in SEQ ID NO: 7.

2. The composition of claim 1, wherein the probe has a 5' terminus labeled with biotin.

3. A DNA microarray for detecting one or more viruses selected from the group consisting of norovirus types I and II, rotavirus G genotype, hepatitis A virus, coxsackievirus, astrovirus, and adenovirus, on which the composition defined in claim 1 is spotted.

4. A kit for detecting one or more viruses selected from the group consisting of norovirus types I and II, rotavirus G genotype, hepatitis A virus, coxsackievirus, astrovirus, and adenovirus, comprising the DNA microarray defined in claim 3.

5. A method of detecting one or more viruses selected from the group consisting of norovirus types I and II, rotavirus G genotype, hepatitis A virus, coxsackievirus, astrovirus, and adenovirus, comprising:
  performing a hybridization reaction on a sample collected from a specimen using the composition defined in claim 1; and
  detecting a hybridized viral nucleic acid.

6. A DNA microarray for detecting one or more viruses selected from the group consisting of norovirus types I and II, rotavirus G genotype, hepatitis A virus, coxsackievirus, astrovirus, and adenovirus, on which the composition defined in claim 2 is spotted.

7. A kit for detecting one or more viruses selected from the group consisting of norovirus types I and II, rotavirus G genotype, hepatitis A virus, coxsackievirus, astrovirus, and adenovirus, comprising the DNA microarray defined in claim 6.

8. A method of detecting one or more viruses selected from the group consisting of norovirus types I and II, rotavirus G genotype, hepatitis A virus, coxsackievirus, astrovirus, and adenovirus, comprising:
  performing a hybridization reaction on a sample collected from a specimen using the composition defined in claim 2; and
  detecting a hybridized viral nucleic acid.

\* \* \* \* \*

SEQUENCE LISTING

```
<160> NUMBER OF SEQ ID NOS: 7

<210> SEQ ID NO 1
<211> LENGTH: 57
<212> TYPE: DNA
<213> ORGANISM: Artificial
<220> FEATURE:
<223> OTHER INFORMATION: probe for Norovirus type I

<400> SEQUENCE: 1
ggacaggaga tcgcaatctc ctgcccgaat tygtaaatga tgatggcgtc taaggac        57

<210> SEQ ID NO 2
<211> LENGTH: 61
<212> TYPE: DNA
<213> ORGANISM: Artificial
<220> FEATURE:
<223> OTHER INFORMATION: probe for Norovirus type II

<400> SEQUENCE: 2
ctatgttccc ccayataata gtrgatgtta ggcaaytgga acctgtgttg atccccttac     60
```

-continued c                                                                  61

<210> SEQ ID NO 3
<211> LENGTH: 60
<212> TYPE: DNA
<213> ORGANISM: Artificial
<220> FEATURE:
<223> OTHER INFORMATION: probe for Rotavirus

<400> SEQUENCE: 3
rtgtamwsaa tatatwaaya myggkytrcc accaatkcar aatacdagra atrtwgtwcc     60

<210> SEQ ID NO 4
<211> LENGTH: 52
<212> TYPE: DNA
<213> ORGANISM: Artificial
<220> FEATURE:
<223> OTHER INFORMATION: probe for HAV

<400> SEQUENCE: 4
ctggvagrtt ggtgagrktb aatgatgaaa aatggacaga aatgaaagat ga             52

<210> SEQ ID NO 5
<211> LENGTH: 59
<212> TYPE: DNA
<213> ORGANISM: Artificial
<220> FEATURE:
<223> OTHER INFORMATION: probe for Coxsackievirus

<400> SEQUENCE: 5
ggcaracdtc cacraaycch agygtbttyt ggacagargg daatgcmcca ccvmgbatg      59

<210> SEQ ID NO 6
<211> LENGTH: 59
<212> TYPE: DNA
<213> ORGANISM: Artificial
<220> FEATURE:
<223> OTHER INFORMATION: probe for Astrovirus

<400> SEQUENCE: 6
gaggatacya grgtrataca yataactgca actgaraara ayacwgattc hacvccwgc      59

<210> SEQ ID NO 7
<211> LENGTH: 50
<212> TYPE: DNA
<213> ORGANISM: Artificial
<220> FEATURE:
<223> OTHER INFORMATION: probe for Adenovirus

<400> SEQUENCE: 7
sawaccagcc cmatgywrcc atgytayggg tcwtacgcya raccaacaaa                50